United States Patent [19]
Brazdil, Jr. et al.

[11] Patent Number: 5,895,635
[45] Date of Patent: Apr. 20, 1999

[54] PROCESS FOR RECOVERY AND RECYCLE OF AMMONIA FROM AN ACRYLONITRILE REACTOR EFFLUENT STREAM USING AN AMMONIUM PHOSPHATE QUENCH SYSTEM

[75] Inventors: James Frank Brazdil, Jr., Highland Heights; Kenneth Paul Keckler, Lima; Richard Paul Hauser, Ravenna, all of Ohio

[73] Assignee: The Standard Oil Company, Cleveland, Ohio

[21] Appl. No.: 08/955,559

[22] Filed: Oct. 17, 1997

Related U.S. Application Data

[63] Continuation of application No. 08/640,193, Apr. 30, 1996, abandoned.

[51] Int. Cl.$^6$ .......................... C01C 3/00; C07C 253/00
[52] U.S. Cl. .......................... 423/238; 558/319
[58] Field of Search .......................... 423/235, 237, 423/376, 238; 558/319

[56] References Cited

U.S. PATENT DOCUMENTS

| | | | |
|---|---|---|---|
| 2,797,148 | 6/1957 | Carlson | 23/196 |
| 3,718,731 | 2/1973 | Carlson et al. | 423/238 |
| 3,914,386 | 10/1975 | Anderson | 423/238 |
| 3,985,863 | 10/1976 | Rice et al. | 423/352 |
| 4,036,870 | 7/1977 | Castellion et al. | 260/465.3 |
| 4,287,162 | 9/1981 | Scheibel | 423/238 |
| 4,918,214 | 4/1990 | Brazdil, Jr. et al. | 558/319 |

FOREIGN PATENT DOCUMENTS

| | | | |
|---|---|---|---|
| 2431531 | 1/1975 | Germany | 423/238 |
| 0222587 | 10/1924 | United Kingdom . | |

*Primary Examiner*—Wayne Langel
*Attorney, Agent, or Firm*—Michael F. Esposito; David J. Untener

[57] ABSTRACT

A process for the recovery of unreacted ammonia from the reactor effluent obtained from a reaction zone used to produce acrylonitrile or methacrylonitrile comprising quenching the reactor effluent with an aqueous solution of ammonium phosphate wherein the ratio of ammonium ions to phosphate ions in the solution is between about 0.7 to about 1.3, preferably between about 0.9 to 1.2.

18 Claims, 2 Drawing Sheets

PROCESS FOR RECOVERY AND RECYCLE OF AMMONIA FROM AN ACRYLONITRILE REACTOR EFFLUENT STREAM USING AN AMMONIUM PHOSPHATE QUENCH SYSTEM

This is a continuation of application Ser. No. 08/640,193 filed on Apr. 30, 1996, abandoned.

BACKGROUND OF THE INVENTION

Field of the Invention

The present invention relates to a process for the recovery and regeneration of ammonia contained in the effluent obtained from a reaction zone where ammonia and oxygen are reacted with a paraffin to produce the corresponding aliphatic nitrile. In particular, the present invention relates to the recovery and regeneration of unreacted ammonia contained in the effluent passing from a reaction zone wherein ammonia and oxygen are reacted with (1) propane to produce acrylonitrile or (2) isobutane to produce methacrylonitrile.

U.S. Pat. Nos. 3,936,360 and 3,649,179 are each directed to a process for the manufacture of acrylonitrile utilizing propylene, oxygen and ammonia as the reactants. These gases are passed over a catalyst in a fluid bed reactor to produce acrylonitrile which passes from the reactor to a recovery and purification section. This reaction also has some unreacted ammonia which is typically removed from the process by treatment in the quench column with an acid. The '179 patent discloses that the quench acid may be either sulfuric, hydrochloric, phosphoric or nitric acid. The '360 patent teaches the use of sulfuric acid in the quench to remove the unreacted ammonia. In the manufacture of acrylonitrile using propylene as the hydrocarbon source, the preferred embodiments clearly utilize sulfuric acid with the resulting formation of ammonium sulfate. Typically, the ammonium sulfate is either recovered and sold as a co-product (fertilizer) or may be combined with other heavy organics produced in the process and deep-welled for environmentally safe disposal.

Great Britain Patent 222,587 is directed to ammonium recovery from an ammonia-containing gas mixture utilizing an aqueous phosphoric acid solution, an aqueous solution of ammonium hydrogen phosphate ($(NH_4)H_2PO_4$), or mixtures thereof. The ammonia is recovered by heat decomposition and dissolving the resulting residue in water to regenerate the ammonium recovery phosphate solution. This ammonia recovery process is directed to the recovery of ammonia from coal gas or coke ovens at temperatures of 50° C. to 70° C.

U.S. Pat. Nos. 2,797,148 and 3,718,731 are directed to the recovery of ammonia from a process stream used in the production of HCN. The process of recovery uses an ammonium phosphate solution to capture the ammonia and then uses steam stripping to regenerate the ammonia from the ammonium phosphate solution. Typically, the process is operated by contacting the ammonia-containing gas with a 25% to 35% by weight ammonium phosphate solution having a pH of about 6 at a temperature of between 55° C. to 90° C. Ammonia regeneration is affected by contacting the resulting ammonium phosphate solution with steam. The processes in each of these patents disclose that the ammonium ion/phosphate ion ratio is at least 1.2 or greater.

The process of the present invention is advantaged over the prior art practice used in propylene ammoxidation because it avoids the formation of an ammonium salt-containing waste stream that must either be (1) treated to recover the ammonium salt or (2) disposed of in an environmentally safe manner. Rather, the process of the present invention results in the recovery of ammonia and regeneration of the ammonium phosphate quench solution by subjecting the quench solution to elevated temperatures and pressure in order to decompose the ammonium phosphate salt. The quench system of the present invention results in additional unexpected advantages in propane ammoxidation compared to propylene ammoxidation to acrylonitrile. Among these advantages are: (1) complete capture of by-product acrolein, thus enhancing product recovery efficiency by minimizing loss of product through, for example, reaction of acrolein with HCN in the product separation and recovery train of the process, (2) lower TOC (Total Organic Carbon) in the quench bottoms, (3) higher percentage of organics present in the quench bottoms are present as strippable/recoverable monomers instead of unrecoverable waste polymers and (4) the ability to use a lower severity waste organic treatment (e.g., wet oxidation) because of the presence of lower TOC and polymers in the quench bottoms solution. A further significant advantageous feature of the process of the present invention is that all the waste water streams may be readily handled by conventional biotreatment processes unlike the waste streams associated with propylene ammoxidation to manufacture acrylonitrile.

SUMMARY OF THE INVENTION

It is the primary object of the present invention to provide the process for the recovery or regeneration of ammonia contained in the effluent from a reactor zone where an ammonia, oxygen and propane/isobutane are reacted to produce acrylonitrile/methacrylonitrile.

It is another object of the present invention to avoid the necessity for disposing of excess ammonia which results from the ammoxidation of propane to acrylonitrile.

It is still another object of the present invention to recover ammonia from a propane ammoxidation reaction without any significant loss of ammonia.

Other objects as well as other aspects and features and advantages of the present invention will become apparent for those from consideration of the specification including the drawings and the claims.

To achieve the foregoing objects and in accordance with the purpose of the present invention as embodied and broadly described herein, the process of recovering unreacted ammonia from the effluent obtained from a reactor zone wherein oxygen, ammonia and a hydrocarbon selected from the group consisting of propane and isobutane are reacted in the presence of an ammoxidation catalyst at an elevated temperature to produce the corresponding nitrile comprises (1) quenching the fluid bed reactor effluent containing the corresponding nitrile and unreacted ammonia with a first aqueous ammonium phosphate quench solution wherein the ratio of ammonium ions ($NH_4^+$) to phosphate ions ($PO_4^{-3}$) is at least about 0.7 but not more than about 1.3, thereby absorbing ammonia to form a second aqueous ammonium phosphate solution richer in ammonium ($NH_4^+$) ions than the first solution, (2) heating the second solution to an elevated temperature to reduce the amount of ammonium ions present in the second solution back to substantially the same level present in the first solution and generate a vaporous stream containing ammonia, recycling said vaporous stream containing ammonia to the ammoxidation reaction zone.

In a preferred embodiment of the process of the present invention, the second aqueous ammonium phosphate solution is treated by means of a stripping gas to remove substantially all of the acrylonitrile and other useful co-products from the second solution prior to heating the solution to decrease the $NH_4^*$ ion content.

In another preferred embodiment of the present invention, the stripper gas containing acrylonitrile is recycled for recovery and purification of the acrylonitrile.

In a further preferred embodiment of the present invention the second solution after stripping and ammonia removal is transferred to a wet oxidation reactor whereby the solution is subjected to wet oxidation at an elevated temperature and pressure to remove any heavy organics contained in the quench solution.

In a still further preferred embodiment of the present invention, the second solution after ammonia removal is transferred to an evaporator to remove excess water from the ammonium phosphate solution which is then recycled for use in the quench.

Preferably, the temperature of the first solution is between 40° C. and 80° C., especially preferred being 50° C. to 65° C.

Typically, the first quench solution has an ammonium/ phosphate ratio of between 0.7 to about 1.3, preferably between about 0.9 to about 1.2 with especially preferred being between about 1.0 and about 1.2. The resulting pH of the first quench solution is between 2.8 and about 6. The phosphate ion concentration in the first quench solution can be up to 40% by weight preferably up to about 35% by weight.

DETAILED DESCRIPTION OF THE INVENTION

Figure 1:
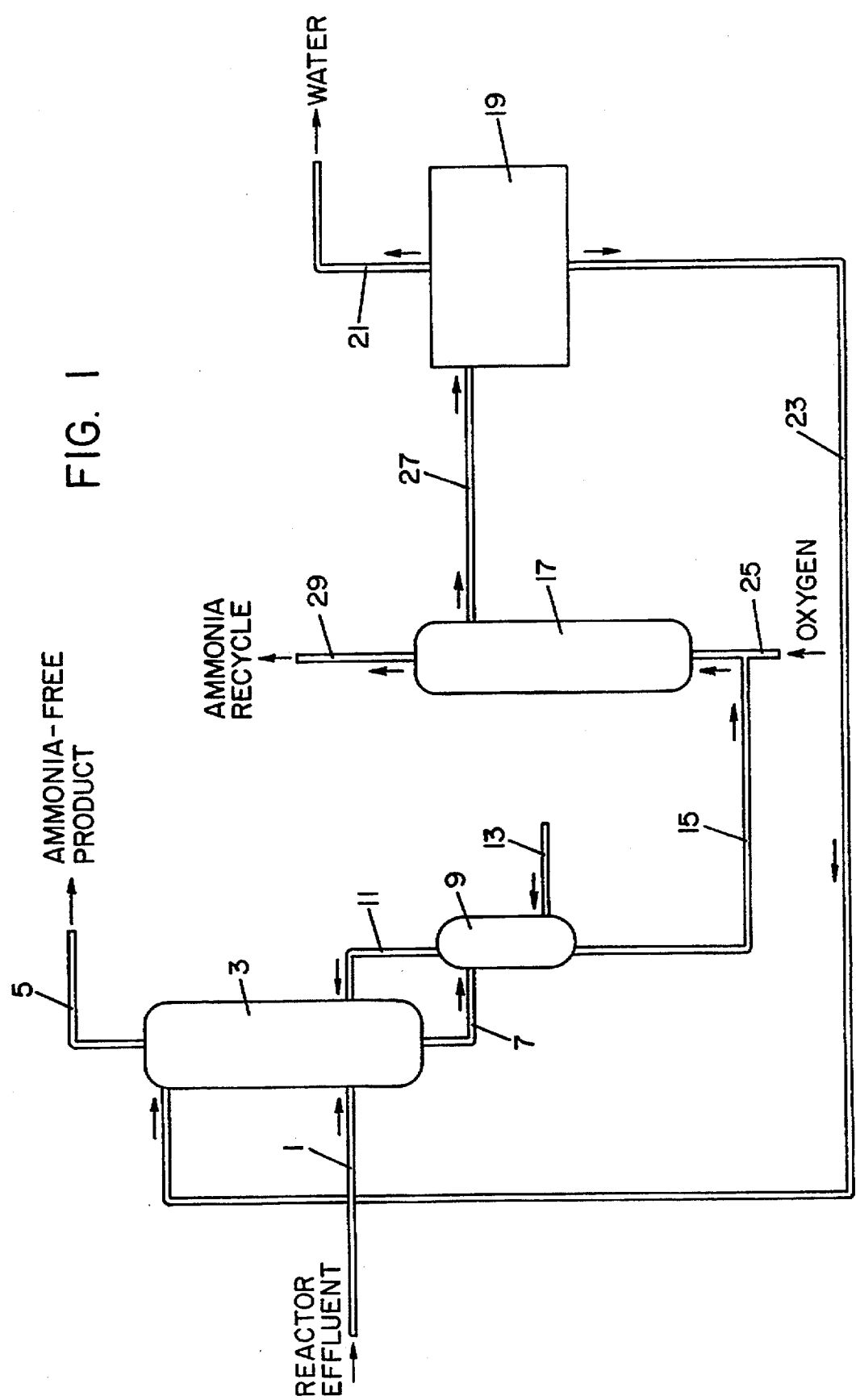
FIG. 1 is a flow diagram of a preferred embodiment of the present invention.

Reference will now be made in detail to the present preferred embodiments of the present invention.

The present invention is directed to a process of quenching the effluent obtained from a propane ammoxidation reaction zone. Preferably, the reaction takes place in a fluid bed reactor although other types of reactors such as transport line reactors are envisioned as suitable in the practice of the invention. Fluid bed propane ammoxidation reaction conditions and fluid bed catalyst useful in propane ammoxidation are known in the art as evidenced by U.S. Pat. No. 4,746,641 assigned to the assignee of the present application and herein incorporated by reference. The novel process of the present invention comprises quenching the reactor effluent obtained from the reaction of ammonia, oxygen and propane in a reaction zone (e.g. fluid bed reactor) to produce acrylonitrile with a first aqueous ammonium phosphate solution having a ratio of ammonium ions to phosphate ions of at least 0.7 but not more than 1.3, thereby absorbing ammonia to make a second ammonium phosphate solution richer in ammonium ions than the first solution, heating the second solution to an elevated temperature to reduce the ammonium ion content in the second solution back to substantially the same ammonium ion content present in the first solution and generate a vaporous stream containing ammonia and water, increasing the molar concentration of ammonia in this vapor stream.

and recycling the vaporous stream containing ammonia to the fluid bed reactor.

Preferably the ammonium ion/phosphate ion ratio is between about 0.9 and about 1.2, especially preferred being abut 1.0 to 1.2. The temperature of the first quench solution is usually between 40° C. to about 80° C., preferably between about 50° C. to 65° C., especially preferred being about 55° C. to about 60° C.

The pH of the first (original) quench solution should be maintained between about 2.8 to no greater than 6.0, preferably between 2.8 to about 5.8.

Preferably, the original quench solution comprises a mixture of a monoammonium phosphate/phosphoric acid aqueous solution (90% monoammonium phosphate-10% $H_3PO_4$) although a lean aqueous monoammonium phosphate solution is also envisioned as suitable in the practice of the present invention. When the aqueous monoammonium phosphate solution is utilized, the unreacted ammonium present in the reactor effluent is absorbed to convert the monoammonium phosphate to diammonium phosphate.

During the quench procedure, the products (acrylonitrile, acetonitrile and HCN) are removed as overheads and are substantially free of ammonia. The quench solution bottom containing the diammonium phosphate also contains residual monomers (e.g. acrylonitrile) in small quantities. These monomers are, preferably, stripped and returned to the quench for further recovery and purification. Typical stripping gases for removal of the residual monomers from the quench bottoms comprise propane, nitrogen, carbon dioxide and carbon monoxide or mixtures thereof.

The quench bottoms solution stripped of useful monomers are then regenerated at an elevated temperature and pressure to convert the diammonium phosphate back to monoammonium phosphate with the release of ammonia. The ammonia is captured as a vapor stream which contains water. This ammonia-rich vapor stream is heated to remove substantially all the water and the ammonia is then recycled back to the reactor. The monoammonium phosphate is recovered and recycled back into the quench column.

In a further preferred embodiment of the present invention, the stripped quench bottom containing the diammonium phosphate is passed through a wet oxidation reactor where it is treated under typical wet oxidation conditions to remove any polymers formed during the ammoxidation process.

In a further preferred embodiment of the present invention, the stripped quench bottom containing unrecoverable monomers and diammonium phosphate is separately treated in a phosphate decomposing unit which separates the diammonium phosphate from the residual monomers. The diammonium phosphate is then regenerated back to the monoammonium phosphate in a separate unit while the residual polymers are transferred to a wet oxidation unit for wet oxidation under conventional temperatures and pressure to produce harmless by-products such as carbon dioxide and water.

Figure 2:
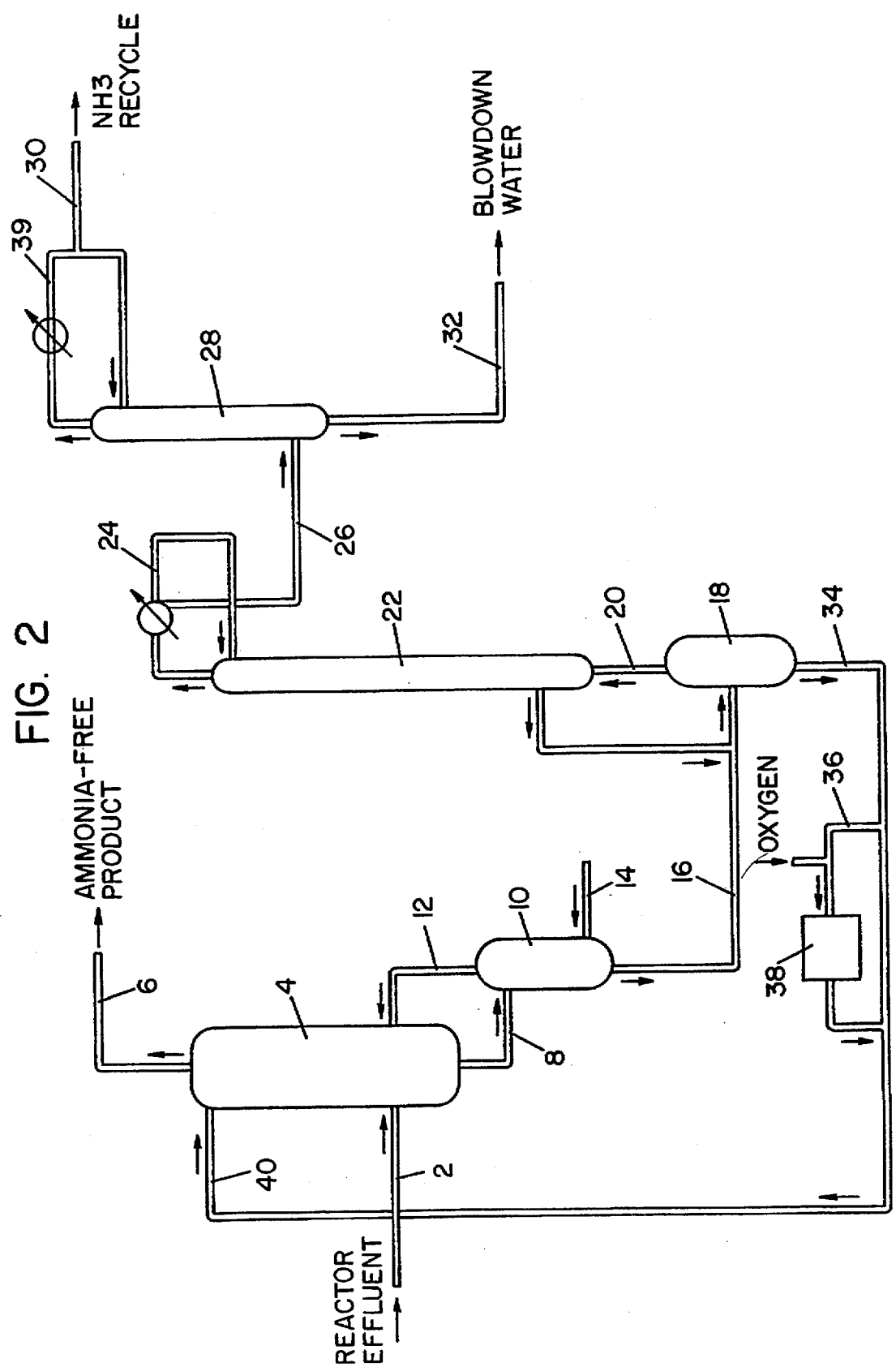
FIG. 2 is a flow diagram of another preferred embodiment of the present invention.

Reference will now be made to FIGS. 1 and 2 which are illustrated of the present preferred embodiments of the process of the present invention as applied to propane ammoxidation.

Referring to FIG. 1, reactor effluent obtained by the direct reaction of propane, ammonia and oxygen in the fluid bed reactor (not shown) over a fluid bed ammoxidation catalyst is passed via line 1 into quench column 3. In quench column 3, the reactor effluent containing product acrylonitrile and unreacted ammonia is contacted with a lean ammonium/ phosphate quench solution which strips unreacted ammonia from the effluent producing an ammonia-free product overhead stream containing crude acrylonitrile. The crude acrylonitrile passes overhead via line 5 into conventional recovery and purification sections (not shown) for subsequent recovery of commercially pure acrylonitrile, crude acetonitrile and hydrogen cyanide. Examples of conventional recovery and purification procedures can be found in U.S. Pat. No. 3,936,360 incorporated by reference herein. The quench bottoms leave quench column 3 via line 7 and enter a quench stripper 9. A stripping gas comprising a recycle stream comprising a mixture of propane, carbon monoxide, carbon dioxide and nitrogen is passed via line 13 into stripper 9 to remove any residual acrylonitrile, acetonitrile or hydrogen cyanide contained in the quench bottoms. The overhead stripper gas 13 containing these residual monomers is recycled back into quench column 3 via line 11 for further recovery of useful products. The stripped quench bottoms are passed from stripper 9 via line 15 into a wet oxidation reactor 17 wherein oxygen is passed via line 25 and a conventional catalytic wet oxidation take place to remove unwanted impurities such as polymers. In addition, the diammonium phosphate contained in the quench stripper bottoms is heated to free the ammonia and convert the diammonium phosphate in solution to monoammonium phosphate. The monoammonium phosphate solution is passed from reactor 17 via line 27 into evaporator 19 where excess water is removed from the solution. This excess water is passed from evaporator 19 via line 21 for recycle or disposal. The concentrated weak monoammonium phosphate solution is passed from evaporator 19 via line 23 for recycle into quench column 3. The ammonia released during the heat treatment in wet oxidation reactor 17 is passed from reactor 17 via line 29 for recycle directly into the fluid bed reactor (not shown).

Typical wet oxidation conditions are utilized for the destruction of the unwanted polymers obtained during the process. Typical catalysts for wet oxidation are soluble salts of copper and iron, oxides of copper, zinc, manganese and cerium and noble metals and are well known in the prior art. See for example Ind. Eng. Chem. Res., 1995 Vol 34, Pages 2-48, incorporated by reference herein. The wet oxidation reaction is designed for normal operation. Typically, wet oxidation is run at a pressure of between about 600 to 3000 psia and a temperature of 200° C. to 650° C.

With reference to FIG. 2 a further preferred embodiment of the present invention is described. The process illustrated in FIG. 2 is substantially the same as that of FIG. 1 except that the phosphate decomposition takes place in a separate unit followed by wet oxidation in a different unit. The reactor effluent obtained by the direct ammoxidation of propane, oxygen and ammonia in a fluid bed reactor (not shown) is passed from the fluid bed reactor via line 2 into quench 4. The reactor effluent containing crude acrylonitrile and unreacted ammonia is contacted in quench 4 with an aqueous monoammonium phosphate solution which enters quench 4 via line 40. The phosphate solution removes the unreacted ammonia from the reactor effluent allowing the ammonia-free products (crude acrylonitrile) to pass overhead from quench 4 via line 6. The crude acrylonitrile passing overhead via line 6 is directed to a conventional recovery and purification section for recovery of commercially pure acrylonitrile, crude acetonitrile and HCN. Quench bottoms are passed from quench 4 via line 8 into quench stripper 10 where a stripping gas (having the same composition as described above) enters the lower portion of the bottom stripper 10 via line 14 and passes upward through the quench bottoms to strip the quench bottoms of any useful monomers present in the bottoms such as acrylonitrile, acetonitrile and hydrogen cyanide. The stripper gas containing useful monomers is then passed from stripper 10 overhead via line 12 into quench 4 for further recovery and purification. The stripped quench bottoms move from stripper 10 via line 16 to phosphate decomposer 18. In phosphate decomposer 18, the diammonium phosphate present in the stripped quench bottom is converted to free ammonium and monoammonium phosphate by heating to an elevated temperature (100° C. to 300° C.). Typically, the pressure is between 1 to 5 atmospheres (atmospheric to 75 psia). Oxygen may be present but is not required. The resulting monoammonium phosphate solution is passed from decomposer 18 via line 34 for recycle via line 40 into quench 4. The free ammonia generated during phosphate conversion in reactor 18 is passed via overhead line 20 into an ammonia rectification unit 22 wherein the free ammonia is purified and passed on to ammonia stripper 28 via line 26 to recover the ammonia for recycle into the reactor (not shown) for manufacture of acrylonitrile or may be recycled via line 24 to rectification unit 22 prior to going to ammonia stripper 28. Water is recovered from ammonia stripper unit 28 and passed via line 32 for recycle or disposal. The $NH_3$ is passed from stripper 28 via line 30 for recycle or is passed via line 39 to stripper 28 for processing prior to entry into line 30 for recycle. The weak monoammonium phosphate solution passed from decomposer 18 via line 34 may be sent through wet oxidation unit 38 via line 36 for removal of polymers and conversion of these unwanted materials into harmless by-products such as hydrogen, carbon monoxide and carbon dioxide.

As described previously, the wet oxidation may be performed under conventional conditions known in the art.

While the invention has been described in conjunction with specific embodiments herein, it is evident that many alternatives, modifications and variations will be apparent to those skilled in the art in light of the foregoing description. Accordingly it is intended to embrace all such alternatives and modifications in variations as for within the spirit and broad scope of the appended claims.

What is claimed is:

1. A process for the recovery of unreacted ammonia from a reactor effluent obtained from a reaction zone, said process consisting essentially of reacting oxygen, ammonia and a hydrocarbon selected from the group consisting of propane and isobutane at an elevated temperature in the presence of an ammoxidation catalyst to produce a corresponding unsaturated nitrile, quenching the reactor effluent containing the corresponding nitrile and unreacted ammonia with a first aqueous ammonium phosphate solution wherein the ratio of ammonium ions ($NH_4^+$) to phosphate ions ($PO_4^{-3}$) is between about 0.7 to about 1.3 to absorb substantially all of the unreacted ammonia present in the reactor effluent to form a second aqueous ammonium phosphate solution richer in ammonium ions than the first solution, heating the second solution to an elevated temperature sufficient to reduce the amount of ammonium ions in the second solution back to substantially the same level present in the first solution and generate a vaporous stream containing ammonia, and recycling the vaporous stream containing ammonia to the reaction zone.

2. The process of claim 1 wherein the hydrocarbon is propane.

3. The process of claim 1 wherein the ammonium ion to phosphate ion ratio in the first solution is between about 0.9 to about 1.2.

4. The process of claim 3 wherein the ammonium ion to phosphate ion ratio in the first solution is between about 1.0 to 1.2.

5. The process of claim 1 wherein a stripper gas is passed through the second ammonium phosphate solution to remove substantially all of the remaining corresponding nitrile from the second solution prior to heating the second solution to the elevated temperature.

6. The process of claim 5 wherein the hydrocarbon is propane.

7. The process of claim 1 wherein the second solution containing substantially the same level of ammonium ions present in the first solution is recycled for use in the quench step.

8. The process of claim 7 wherein the second solution prior to recycle is subjected to wet oxidation to remove any unwanted impurities.

9. The process of claim 5 wherein the heating of the second solution to an elevated temperature takes place in a wet oxidation reactor at wet oxidation conditions to simultaneously remove unwanted impurities from the second solution and reduce the ammonium ion concentration in the second solution to substantially the same level present in the first solution.

10. The process of claim 5 wherein the ammonium ion to phosphate ion ratio in the first solution is between about 0.9 to about 1.2.

11. The process of claim 10 wherein the ammonium ion to phosphate ion ratio in the first solution is between about 1.0 to about 1.2.

12. The process of claim 1 wherein the pH of the first solution is between about 2.8 to 6.0.

13. The process of claim 12 wherein the pH of the first solution is between about 2.8 to about 5.8.

14. The process of claim 5 wherein the pH of the first solution is between about 2.8 to about 6.0.

15. The process of claim 14 wherein the pH of the first solution is between about 2.8 to about 5.8.

16. The process of claim 1 wherein the temperature of the first solution is between 40° C. to 80° C.

17. The process of claim 1 wherein the first solution comprises an aqueous solution comprising monoammonium phosphate and phosphoric acid.

18. The process of claim 5 wherein the first solution comprises an aqueous solution comprising monoammonium phosphate and phosphoric acid.

* * * * *